(12) United States Patent
Marrouche et al.

(10) Patent No.: US 9,028,470 B2
(45) Date of Patent: May 12, 2015

(54) IMAGE-GUIDED RENAL NERVE ABLATION

(75) Inventors: Nassir F. Marrouche, Park City, UT (US); Dennis L. Parker, Centerville, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 319 days.

(21) Appl. No.: 13/525,082

(22) Filed: Jun. 15, 2012

(65) Prior Publication Data

US 2013/0023862 A1 Jan. 24, 2013

Related U.S. Application Data

(60) Provisional application No. 61/498,521, filed on Jun. 17, 2011.

(51) Int. Cl.
A61N 7/02 (2006.01)
A61B 18/00 (2006.01)
A61B 19/00 (2006.01)

(52) U.S. Cl.
CPC ......... *A61N 7/02* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2019/5236* (2013.01)

(58) Field of Classification Search
None
See application file for complete search history.

(56) References Cited

U.S. PATENT DOCUMENTS

| | | | |
|---|---|---|---|
| 4,638,436 A * | 1/1987 | Badger et al. ................. 607/102 |
| 5,769,790 A | 6/1998 | Watkins et al. |
| 6,086,535 A * | 7/2000 | Ishibashi et al. ............... 600/439 |
| 6,451,044 B1 * | 9/2002 | Naghavi et al. .................. 607/96 |
| 6,516,211 B1 * | 2/2003 | Acker et al. .................... 600/411 |
| 6,623,430 B1 * | 9/2003 | Slayton et al. ................ 600/439 |
| 7,162,303 B2 * | 1/2007 | Levin et al. ...................... 607/44 |
| 7,937,143 B2 * | 5/2011 | Demarais et al. ............... 604/21 |
| 8,137,274 B2 * | 3/2012 | Weng et al. .................... 600/437 |
| 8,277,398 B2 * | 10/2012 | Weng et al. ........................ 601/2 |
| 8,295,912 B2 * | 10/2012 | Gertner ......................... 600/426 |
| 8,469,904 B2 | 6/2013 | Gertner |
| 8,512,262 B2 | 8/2013 | Gertner |
| 8,517,962 B2 | 8/2013 | Gertner et al. |
| 2006/0058642 A1 | 3/2006 | Franconi et al. |
| 2007/0167773 A1 | 7/2007 | Jeong et al. |
| 2008/0213331 A1 | 9/2008 | Gelfand et al. |
| 2008/0312561 A1 | 12/2008 | Chauhan |
| 2009/0275821 A1 | 11/2009 | Mallozzi et al. |
| 2010/0057150 A1 | 3/2010 | Demarais et al. |
| 2010/0217114 A1 | 8/2010 | Zhou et al. |
| 2010/0222854 A1 | 9/2010 | Demarais et al. |
| 2013/0225973 A1 | 8/2013 | Gertner |
| 2013/0253381 A1 | 9/2013 | Gertner |

* cited by examiner

*Primary Examiner* — Brian T Gedeon
(74) *Attorney, Agent, or Firm* — James W. Hill; Mark Bentley; McDermott Will & Emery LLP (57) ABSTRACT

A method of treating hypertension in a mammal is described, including: by focused sound energy, heating at least one nerve at a surface of a renal artery in a mammal; during the heating and by magnetic resonance imaging, repeatedly determining thermal levels in each of first and second volumetric zones of a region that includes at least a portion of the surface, the second zone being adjacent to the first zone; after determining that an indicium of a thermal level in the first zone exceeds a first threshold, and upon determining that an indicium of a thermal level in the second zone exceeds a second threshold, ceasing the heating of the at least one nerve for at least three months; and as a result of the heating, lowering a blood pressure in the mammal.

18 Claims, 7 Drawing Sheets

IMAGE-GUIDED RENAL NERVE ABLATION

RELATED APPLICATIONS

This application claims priority, pursuant to 35 U.S.C. §119, to U.S. Provisional Patent Application No. 61/498,521, filed Jun. 17, 2011, titled IMAGE-GUIDED RENAL NERVE ABLATION.

FIELD

The subject technology relates to treatment of hypertension, including by ablation of renal nerves.

SUMMARY

According to embodiments, disclosed is a method of treating hypertension in a mammal, comprising: by focused sound energy, heating at least one nerve at a surface of a renal artery in a mammal; during the heating and by magnetic resonance imaging, repeatedly determining thermal levels in each of first and second volumetric zones of a region that includes at least a portion of the surface, the second zone being adjacent to the first zone; after determining that an indicium of a thermal level in the first zone exceeds a first threshold, and upon determining that an indicium of a thermal level in the second zone exceeds a second threshold, ceasing the heating of the at least one nerve for at least three months; and as a result of the heating, lowering a blood pressure in the mammal.

According to embodiments, the first zone is substantially concentric with the second zone. According to embodiments, the first zone comprises a pathway along which focused sound energy is provided during a span of time. According to embodiments, the first zone comprises a plurality of points on an exterior region of an artery. According to embodiments, the first zone may be around the outside of an artery.

According to embodiments, the magnetic resonance imaging comprises a proton resonance frequency acquisition sequence. According to embodiments, the first and second thresholds are different from each other. According to embodiments, the heating is ceased for at least 5 days, 10 days, 30 days, 60 days, 180 days, four months, six months, or 12 months.

According to embodiments, disclosed is a method of treating hypertension in a mammal, comprising: by focused sound energy, heating a first region of at least one nerve at a surface of a renal artery in a mammal; during the heating and by magnetic resonance imaging, repeatedly determining thermal levels in each of first and second volumetric zones of the first region that includes at least a portion of the surface, the second zone being adjacent to the first zone; after determining that an indicium of a thermal level in the first zone exceeds a first threshold, and upon determining that an indicium of a thermal level in the second zone exceeds a second threshold, heating a second region of the at least one nerve by focused sound energy; during the heating and by magnetic resonance imaging, repeatedly determining thermal levels in each of third and fourth volumetric zones of the second region that includes at least a portion of the surface, the fourth zone being adjacent to the third zone; after determining that an indicium of a thermal level in the third zone exceeds a third threshold, and upon determining that an indicium of a thermal level in the fourth zone exceeds a fourth threshold, ceasing the heating of the at least one nerve for at least three months; and as a result of the heating, lowering a blood pressure in the mammal.

According to embodiments, disclosed is a system for performing renal nerve ablation, comprising: a HIFU device comprising at least one ultrasound transducer and configured to heat a targeted tissue at a focal region of the array; and a MRI device programmed to monitor thermal levels in a plurality of volumetric zones.

According to embodiments, the at least one volumetric zones comprises a first zone and a second zone. According to embodiments, the first zone is substantially concentric with the second zone. According to embodiments, the MRI device comprises at least one of a coil that generates a static magnetic field, a RF coil, an x-gradient coil, a y-gradient coil, and a z-gradient coil. One or more coils allow sequences of currents to acquire PRF measurements and sequences to acquire T1 weighted images. One or more coils allows sequences of currents to acquire MRI images.

One or more of several MRI methods may be used for measuring thermal levels using well-known MRI parameters, such as the spin-lattice relaxation time ("T1"). Sequence parameters—such as the time to repeat ("TR"), the time to echo ("TE"), and the flip angle—may be chosen by the user. For example, thermal level maps can be generated based on such procedures that provide T1 derived images evaluated with fast spoiled gradient echo sequences applied during the actual thermal therapy exposure. The parameters used are to some degree based on the tissue type and the precise evaluation of the behavior due to physiological or metabolic changes in the tissue during thermal therapy exposure. For example, TE, TR, and the flip angle of the spoiled gradient echo may be specified in the sequence. Sequence parameters may be used to localize the low-thermal level elevation induced by a focused ultrasound beam during both the planning and treatment.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this specification, illustrate aspects of the subject technology and together with the description serve to explain the principles of the subject technology.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

According to some embodiments, an apparatus and method for using MRI-guided focused ultrasound to ablate sympathetic nerves near the renal arteries may be employed to allow reduction of blood pressure.

According to some embodiments, the device may comprise MRI-compatible focused ultrasound transducer that can be steered either electronically or mechanically or both. The device may be used to focus energy at points of interest. For example, a target for the device may include the sympathetic nerves that control the blood flow to the kidneys and cause an increase in systemic blood pressure.

Tissues can be destroyed by heat. It has further been discovered that the control of heat was improved by using short pulses such that the effect of blood perfusion is made negligible.

According to some embodiments, provided are devices and procedures to focus high intensity, ultrasonic acoustic waves into the tissue. High-intensity focused ultrasound ("HIFU") is a highly precise medical procedure using high-intensity focused ultrasound to heat and destroy tissue.

Therapeutic ultrasound may be provided as minimally invasive or non-invasive. Further, it may be provided transcutaneously, subcutaneously, intravascularly, inter alia. The ultrasound beam can be focused geometrically, for example with a lens or with a spherically curved transducer, or electronically, by adjusting the relative phases of elements in an array of transducers (a "phased array"). By dynamically adjusting the electronic signals to the elements of a phased array, the beam can be steered to different locations, and aberrations due to tissue structures can be corrected. For example, an ultrasound beam may be localized prior to treatment using a form of MRI acoustic radiation force imaging ("MR ARFI").

As an acoustic wave propagates through the tissue, at least part of it is absorbed and converted to heat. With focused beams, a very small focus can be achieved deep in tissues. When hot enough, the tissue is thermally coagulated. By focusing at more than one place or by scanning the focus, a volume of tissue can be thermally ablated.

In HIFU therapy, ultrasound beams are focused on targeted tissue, and due to the significant energy deposition at the focus, temperature within the tissue rises, destroying the diseased tissue by coagulation necrosis. Each sonication of the beams treats a precisely defined portion of the targeted tissue. The entire therapeutic target is treated by moving the applicator in order to juxtapose multiple shots, according to a protocol designed by the physician. This technology can achieve precise ablation of diseased tissue.

For example, a phased-array of piezoelectric transducers may be used. The heat may be applied to the tissue in a pulsed or continuous wave mode. The energy creates a heat focus that heats either at the tip of an optical fiber, or at the focal region of a transducer or transducers, depending on the heat source.

Medical researchers have discovered that the heat-resistance of cancer cells is poorer than that of normal cells. When the temperature is above 42.5 degrees centigrade, the cancer cells die within 30 minutes while the normal cells are injured slightly and the injury is reversible. According to this characteristic of cancer cells, a high-intensity focused ultrasound tumor therapeutic system makes use of ultrasound waves as energy source and their penetrability and focusing, and delivers the ultrasound waves with a relatively low average intensity level emitting from the applicator coupled by medium through skin into the tumor tissue within human body. These ultrasound beams within tissue are focused at a spatial focal spot and a focal region (with a size of about 3 mm*8 mm) with an average acoustic intensity level of over 1000 W/m$^2$ is formed. The temperature at the focal region instantaneously (0.1 to 5 seconds) has a sharp rise (beyond 43 degrees centigrade). By this thermal effect together with its mechanical action, the disruption of the tissue at the focal region can be achieved. The cancer cells can be exposed by the focal region through the scanning way from point to line, then from line to slice and then from slice to solid and finally the whole tumor tissue is cauterized and the therapeutic purposes is realized.

With the development of ultrasound therapy, great improvements on checking and treating tumors and other tissue by ultrasound therapy associated with imaging devices, such as B-mode ultrasound have been achieved. The B-mode ultrasound imaging apparatus used in the existing ultrasound therapy equipments is mainly used to locate and observe tissue prior to ultrasound therapy. By use of MRI or CT checking for some time after treatment, the existing equipments determine if the needed therapeutic dosage has been achieved at the target area after treatment, if the coagulative necrosis of target tissue is caused, and evaluate the therapeutic effects after treatment. In this way, a lot of disadvantages exist because the therapeutic effects cannot be observed in time and the therapeutic dose is controlled only by experiences. If the dose is insufficient, the diseased tissue cannot be destroyed effectively and the therapeutic effects cannot be achieved. If the dose exceeds the needed dose, the normal tissue may be destroyed and there exists a big safety problem. Therefore, the real-time evaluation on the therapeutic effects during treatment becomes very necessary.

The present disclosure relates to a mechanical manipulator for ultrasonic transducers which are under supervisory control by the surgeon through a computer. A multiple probe technique and a custom designed robotic manipulator system are disclosed, that can be used for focusing ultrasound energy in the target tissue in order to position precisely multiple ultrasound transducers to focus into deep targets.

The present disclosure also relates to a mechanical manipulator for HIFU transducers having a plurality of modules for aiming the transducers, including a single diagnostic module and a plurality of treatment modules.

The present disclosure also relates to a mechanical manipulator for ultrasonic transducers having a base harness from which a diagnostic module and a plurality of treatment modules are centrally mounted.

The present disclosure also relates to a mechanical manipulator having a plurality of treatment modules, each of which allows movements in three degrees of freedom under supervisory control of the surgeon through a computer. Each module allows the transducer to move linearly under the control of a first motor, with additional motors controlling the yaw and pitch. Each module is mounted from a vertical rod (serving as a common central axis) so that the transducers are originally aimed to a central focal point.

The present disclosure also relates to a mechanical manipulator for HIFU transducers where a diagnostic probe is originally mounted centrally (it is displaced linearly to acquire multiple images in parallel planes) from a base unit and treatment probes are offset radially from the diagnostic probe.

The present disclosure relates to using a base harness which is mounted on a treatment table. A centrally disposed vertical axis may be adjusted between the legs of the harness in relation to the patient. The vertical axis carries the diagnostic probe which may be adjusted for individual patients. Treatment probes are offset using horizontal arms from the central vertical shaft. The treatment modules are then hung from the horizontal arms by separate vertical shafts. The modules may move in and out toward the central vertical shaft and may move right and left in a yaw movement or up and down in a pitch movement. Motors, preferably one for each axis, may be provided to facilitate this movement in three degrees of freedom. The movement of the motors is controlled using a PC-based controller through a user interface. Alternatively, the device may be positioned manually. The transducers may be moved to focus the ultrasound on a single point or a series of points to cause ablation of tissues.

In order to treat deep-seated abnormalities or other tissue, it is desirable to provide an automated mechanical manipulator system for controlling the movement of the HIFU transducers. By using a computer to control the movement of the transducers in a robotic system, it is possible to carefully control the location of the focused ultrasound transducer (and thereby the lesion produced by it) to ablate the tissue as indicated by the surgeon through the computer. This allows the ultrasound to be carefully controlled through a single, or a set of multiple transducers. The result is a system which has a compact work space while allowing the individual transducers to be moved independently.

During a registration process, a co-ordinate system of such data/images is transferred and related to robot and patient co-ordinates. Registration is followed by a surgical execution step, where the surgeon utilizes the pre-operative plan and is assisted by either a passive (such as a mechatronic tool to hold a device precisely in a given position), or semi-autonomous or autonomous device, such as a robot, to help perform surgical interventions.

This robotic system guides a set of transducers through a predetermined and image-guided trajectory which is set by the surgeon. In one embodiment, the transducers are each mounted on an independent module, each of which is equipped with three degrees of freedom to access any given location in a three-dimensional workspace. The procedure is guided by using a separate diagnostic ultrasound module. This diagnostic module is utilized for pre-surgical planning and may also be used to control the location of the treatment modules during the procedure.

This robotic system allows the use of either single or multiple treatment probes for organotripsy of various tissue types depending on their relative position in the body. This system may also be used for other non-invasive procedures using, for example, lasers or minimally invasive surgical tools. This system is equally suited for other imaging modalities other than diagnostic ultrasound for on-line monitoring and surgical guidance.

In order to ablate selective regions in urological organs, the use of multiple transducers is preferable for a number of reasons. This allows better access to areas which may not be safely reached along a long path alone either due to the deterioration of beam convergence along a long path or due to an access window which is partly inhibited. It also allows the production of adequate dosage using one of two modes. The first mode uses a selective overlapping focal zone by constructive interference to superimpose foci while keeping low dosage exposure in individual beam paths. Another mode is the use of individual HIFU probes or a multiple and selective combination of probes which are controlled and programmed with adequate power to result in individual lesions. This may be advantageous for a faster time of operation (due to the ability of the system to produce multiple lesions simultaneously at selected locations) or to approach larger volume target sites which may not be reachable by a single probe. Further, this arrangement allows the modulation of effective power in the focal region by independently selecting HIFU probe specifications or independently programming the dosage parameters of the probes. This renders the system to be flexible as to lesion shapes and sizes and also provides flexibility in energy distribution and minimizes the effects of non-linear propagation of ultrasound by reducing the possibility of standing waves during continuous exposure routines.

Several types of HIFU transducers have been developed for extra-corporeal, intra-cavitary and on-site/impregnated applications. The latter two can have a very selective approach for fewer targets; however, the extra-corporeal probes offer a preferred choice for completely non-invasive generic targets. An extracorporeal transducer that is a phased array composition of multiple elements may be used. The beam shape and position can be controlled electronically. Alternatively, the acoustic beams may be fixed in shape and in position with respect to the source. Modification of focal size can be achieved by changing the physical properties of the source transducer (i.e., spherical shell aperture or radius of curvature, or lens dimensions or properties). A precisely controlled, mechanical manipulation system is therefore required to move the ultrasound focus (or, joint foci in case of multiple transducers) to the target location(s). The beam-shape is governed by transducer specifications, and thus is immutable during the procedure. The specific location of the tissue/organ in the human body will also affect the design of applicator systems. Based upon the dimensions, location and nature of the abnormality, the size and shape of the applicators (and thus the beam shape) can be evaluated by modeling the ultrasonic field in front of the transducers.

The principle of remote, localized tissue ablation using HIFU comprises sudden thermal necrosis in the focal lobe of the transducer due mainly to the absorption of ultrasound energy. The temperatures thus induced (e.g., about 60-80° C.) produce irreversible changes in the targets. Target temperature thresholds may be any temperature above body temperature. For example, target temperature thresholds may include temperatures equal to or greater than 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C. Thus, instrumentation for precise and accurate targeting of the incident energy is of prime importance in order to ensure that any undesirable exposure in normal tissue is avoided. Thus, it is highly desirable to contrive a very accurate and precise positioning system for the reasons of safety due to the risk of unwanted exposure of overlying normal tissue.

The ultrasound transducers which are used for treatment are coupled through an appropriate liquid such as degassed water. In another embodiment, the transducers are encapsulated in a sealed degassed water bolus with compliant bellows at one end to couple appropriate ultrasound energy with the tissue. The transducers are independently controlled to either work in coordination with each other or to function and control independent trajectories. The surgeon can control and maneuver the treatment modules in two modes either using manual or automated sequences. The end point accuracy is accomplished and tested within ±0.5 mm and the repeatability to within ±0.1 mm.

The mechanical system described above may be controlled using an electronic interfacing hardware with a PC having controller cards and specially designed hardware that interfaces and controls the system. The typical lesion dimensions produced by a single or multiple probes may not be able to cover the entire volume of the desired target region. It is necessary to scan mechanically the superimposed foci mutually over the entire tissue of interest. The treatment is to be carried out by means of a suitable exposure duration of the HIFU beam (at a selected power/intensity level) at one spot following a scanning motion of the probes and subsequent exposure until the entire volume of the target is covered in a three-dimensional manner.

When the transducer is employed to receive the reflected sound (receive mode), the voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

Ultrasound beam scanning as described above comprises a series of measurements in which the steered ultrasonic wave is transmitted, the system switches to its receive mode after a brief time interval, and the reflected ultrasonic wave is received and stored. Typically, transmission and reception are steered in the same direction during each measurement to acquire data from a series of points along an acoustic beam or scan line. The receiver is dynamically focused at a succession of ranges along the scan line as the reflected ultrasonic waves are received.

The positioning system for moving the focal point F of the probe to a desired location allows multiple two-dimensional B-mode images to be acquired by a work-station as a registered set of image slices representing a tissue volume. The imaging volume can then be reformatted as necessary to obtain the views desired. Since the registration of the object (i.e., patient) is fixed to the mechanical positioning system, the probe can be registered to the positioning system. This provides a known mechanical relationship between the probe and the patient. The system operator can then prescribe the tissue volume to be treated by outlining tissue boundaries on a set of ultrasound image slices describing a tissue volume including the tissue volume to be treated. The combined imaging and therapy probe can then be moved by the positioning system to locations within the prescribed outline to deliver treatment to the desired area of each image slice.

Incorporated herein by reference are the following US applications and/or publications: US Pub. No. 2007/0167773, published on Jul. 19, 2007; U.S. Pat. No. 5,769,790, issued on Jun. 23, 1998; US Pub. No. 2008/0312561, published on Dec. 18, 2008.

According to some embodiments, systems and methods for imaging tissue using magnetic resonance imaging ("MRI") techniques may be used. Thus, thermal surgery guided by MRI systems and procedures to selectively destroy tissue in the patient with localized heating may be performed, without adversely affecting tissue to remain substantially unaffected by the procedure.

Ultrasound imaging has been used for both generating and positioning focused ultrasound waves on tissue to be destroyed. MR images are generally better suited for such guidance, since MRI provides excellent images of tissue, and is not limited to "windows" that excludes bones, for example.

MRI systems may be used not only for planning surgery, but also during actual destruction of tissue. MRI systems using separate scanning sequences provide thermal level information and, in addition, also provide tissue information. Thus, the actual thermal level of the tissue can be ascertained using magnetic resonance imaging methods, and the ablation of the tissue can be observed using the MRI system.

The heated region may be imaged with the use of the MRI systems, employing a thermal level sensitive MR pulse sequence to acquire a thermal level "map" that is used basically to assure that the heat is being applied to the tissue and not to the surrounding healthy tissue. This is done by applying a quantity of heat that is insufficient to cause necrosis but is sufficient to raise the thermal level of the heated tissue. The MRI system thermal level map shows whether or not the heat is applied to the previously located tissue. The imaging system is also used in a separate scan sequence to create an image of the tissue intended to be destroyed. Using the imaging system in the prior art, the operator of the apparatus adjusts the placement of the radiation on the site of the tissue to be destroyed. The MR image of the tissue acquired in the separate scan determines in real time if necrosis is occurring and effectively ablating the tissue. However, the monitoring and guiding are provided using separate two-dimensional scan sequences.

When ultrasound beams are used as the heat source, then the focus of the ultrasound beams can be positioned either by mechanically moving the ultrasound generator to move its focal region, or a phased array ultrasound system can be used to manipulate the position of the focal region so that it is within the diseased tissue that is to be destroyed by heating.

Provided is a process for verifying that a sufficient thermal level was reached during each application of ultrasonic energy to kill the target tissue structure, or portion thereof being heated. This can be done by measuring the change in thermal level of the portion of the tissue structure being heated during the heating process using MR imaging techniques.

There are several MRI methods may be used for measuring thermal levels using well-known MRI parameters, such as the spin-lattice relaxation time ("T1"). Sequence parameters—such as the time to repeat ("TR"), the time to echo ("TE"), and the flip angle—may be chosen by the user. For example, thermal level maps can be generated based on such procedures that provide T1 derived images evaluated with fast spoiled gradient echo sequences applied during the actual thermal therapy exposure. The parameters used are to some degree based on the tissue type and the precise evaluation of the behavior due to physiological or metabolic changes in the tissue during thermal therapy exposure. For example, TE, TR, and the flip angle of the spoiled gradient echo may be specified in the sequence. Sequence parameters may be used to localize the low-thermal level elevation induced by a focused ultrasound beam during both the planning and treatment.

A method of measuring thermal level change using MR techniques exploits the thermal level dependence of the proton resonant frequency ("PRF") in water. The thermal level dependence of the PRF is primarily due to thermal level-induced induced rupture, stretching, or bending of the hydrogen bonds in water. The thermal level dependence of pure water is 0.0107 ppm/° C., and the thermal level dependence of other water-based tissues is close to this value.

Changes in PRF are measured by first taking a MR image before the delivery of heat, and subtracting this baseline value from subsequent measurements. Notably, the total imaging time is kept relatively short for the baseline value to remain relatively stable, since drifts in the magnetic field can occur over time.

The thermal level-induced changes in PRF are then estimated by measuring changes in phase of the MR signal, or proton resonance frequency shift ("PRFS") in certain MR imaging sequences.

Various methods for acquiring electromagnetic signals are known, in particular in the magnetic resonance imaging (MRI) field. These methods have common characteristics.

They generally consist in subjecting the body in question to a high-intensity magnetic induction $B_0$, typically between 0.1 and 3 Tesla. The effect of this induction is to orient the magnetic moments of the protons of the hydrogen contained in the water molecules of the body in a direction close to the main direction of the magnetic induction $B_0$.

The body part imaged is then subjected to a radiofrequency wave applied perpendicular to the magnetic induction $B_0$ and the frequency of which is typically adjusted to the Larmor precession frequency of the hydrogen nucleus in the magnetic induction $B_0$ in question. This frequency is proportional to the intensity of the magnetic induction $B_0$ and has the specificity of bringing into resonance the protons of the hydrogen contained in the water molecules of the body. By way of example, for an induction $B_0$ of 1 Tesla, the corresponding Larmor frequency is in the region of 42 MHz.

Immediately after the transmission of this radio frequency wave, the magnetic moments that have been subjected to the wave begin to oscillate around their equilibrium position and again take up a position along their original direction, close to that of the magnetic induction $B_0$. This phenomenon is known as proton relaxation.

During the relaxation, each water proton that has come into resonance creates, as a result, a relatively weak electromagnetic signal, called a magnetic resonance signal. This signal can then be detected by means of an appropriate detection module.

Gradients of the magnetic induction $B_0$ can be used in various spatial directions, so as to have different induction values between two points in space, each corresponding to an elementary volume of the body in question.

The use of magnetic induction $B_0$ gradients therefore allows spatial localization of the signal. The step of coding the space by means of the gradients is carried out between the proton excitation and the magnetic resonance signal reception.

These basic principles give rise to different methods of exploitation so as to allow the production of a selective image for a chosen element of the body observed, for example a blood vessel.

In a first method, referred to as "time of flight" method, the radio frequency waves are transmitted repeatedly and regularly, in a train of pulses. The repetition of these waves is adjusted so as to be sufficiently frequent for the proton relaxation not to have time to be entirely complete before transmission of the next wave. This saturation phenomenon means that the magnetic resonance signal is greatly reduced. It virtually makes it possible to eliminate the signals transmitted by the immobile protons, i.e. typically the protons that are part of tissues of the body in question.

On the other hand, mobile protons that penetrate the zone in question without having been subjected beforehand to a train of pulses come into resonance and create a magnetic resonance hypersignal that can be detected. The mobile protons are typically the protons contained in the water of the circulating blood.

This time of flight method therefore makes it possible to distinguish between the relaxed mobile protons and the saturated immobile protons and thus makes it possible to isolate a selective signal corresponding, for example, to a blood activity. This method can in particular be applied in the field of angiography, since it makes it possible to detect a signal originating from a blood vessel in particular.

The time of flight method is, however, limited to the analysis of blood vessels that are short and have a high flow rate, since, if the opposite is true, the protons contained in the blood circulating in these vessels rapidly undergoes saturation, like the protons of the surrounding tissues.

A second method, referred to as "phase contrast" method, takes advantage of the relationship that exists between the phase of the detected magnetic resonance signal and the rate of proton displacement in the body in question, to allow detection of blood vessels within the body. However, this method has drawbacks insofar as a prior estimation of the rate of circulation in the vessels is necessary. In addition, since the phase is a quantity expressed to within $2\pi$, an ambiguity remains regarding the effective rate deduced from a magnetic resonance signal.

These first two methods are therefore based on characteristics associated with a displacement, in particular of blood in the body. They thus find an application in the angiography field. On the other hand, they do not make it possible to detect a particular static or virtually static element of the body. They cannot therefore be used as a basis for the formation of an image for a particular organ or for a particular cell type.

A third method has made a name for itself in the last few years in the angiography field. It comprises a step consisting in injecting a contrast product into a body. In general, the contrast product used is gadolinium attached to a chelating agent such as DOTA (or tetraazacyclododecane tetraacetate) or DTPA (or diethylenetriamine pentaacetate). The chelating agent is a molecular cage that surrounds the gadolinium and makes it possible to limit its toxicity with respect to the body into which it is injected. The effect of this product is to decrease the relaxation time of the protons that are in proximity. Specifically, the contrast product contains single unpaired electrons which have a paramagnetic effect that acts on the water protons.

This increase in proton relaxation makes it possible to limit the saturation in the zone where the injected product is located. The resulting magnetic resonance signal is therefore greatly increased. Conversely, the protons that are not in immediate proximity to the gadolinium keep an unchanged relaxation time and therefore generate a lower magnetic resonance signal.

Initially after injection, the contrast product moves in the blood vessels without being absorbed by the surrounding tissues. Detection of the magnetic resonance signals therefore makes it possible to distinguish between the blood vessels and the surrounding tissues and also to form an image revealing this distinction.

However, this technique also has drawbacks. In particular, paramagnetic gadolinium, in addition to its action on proton relaxation time, creates magnetic induction microgradients that result in local distortions of the magnetic induction to which the body is subjected. The frequencies of the waves transmitted are dispersed. This effect can result in the loss of certain signals. When the magnetic resonance signals are used to form an image of a zone of the body in question, said image will therefore be difficult to interpret. This results in the spatial resolution of the images obtained by this technique being limited: this method does not allow complete suppression of the signals derived from tissues lacking contrast product.

An object of the present disclosure is to provide a method for acquiring magnetic resonance signals that limits the problems encountered in the above techniques.

Another object of the disclosure is to enable acquisition of the signals from a selected observed zone, independent of its type. For example, the observed zone may contain substantially mobile or substantially immobile protons. It may be a blood vessel or a vascularized network, but also an organ, a group of cells, or the like.

The disclosure thus proposes a method for acquiring electromagnetic signals received from at least one part of a body placed in a system comprising means for generating a magnetic induction $B_0$, said magnetic induction comprising gradients in certain directions in space, means for transmitting radio frequency wave pulse sequences perpendicular to the magnetic induction $B_0$ in a range of adjustable frequencies, and means for detecting electromagnetic signals received from said body part. The method comprises the following steps: a) exciting said body part by means of a radio frequency wave pulse sequence in a range of frequencies adjusted according to the magnetic induction $B_0$ and to a chemical shift for at least some of said radio frequency waves; and b) detecting, coherently with the excitation of step a), electromagnetic signals received from said body part, said signals corresponding substantially to magnetic resonance signals of the protons of the observed zone having undergone the treatment.

The observed zone envisioned here may be of various types, for instance a blood vessel, a group of cells expressing a gene, a nerve or set of nerves, a nerve zone, or the like.

Optionally, the method may further comprise the step of injecting, into said body part, an amount of contrast product capable of being temporarily fixed in or of passing through an observed zone of said body part, said contrast product comprising at least one element capable of causing a chemical shift of a resonance frequency of water hydrogen protons.

The chemical shift provided by the contrast product brings about a shift in the resonance frequency of the hydrogen protons contained in the water in proximity to the injected contrast product. This shift in frequency makes it possible to obtain a selective signal from the protons chemically shifted during a radio frequency-based solicitation taking into account this shift. Such selective signal can advantageously be used as a basis for forming an image.

A contrast product optionally injected into at least one part of a body for the purpose of acquiring electromagnetic signals from said body part comprises at least one element capable of causing a chemical shift of a resonance frequency of water hydrogen protons. The element included in the contrast product may advantageously be a lanthanide, for example dysprosium, praseodymium, and/or europium, optionally attached to a chelating agent, or any other element capable of inducing a modification of the resonance frequency.

According to the disclosure, an amount of contrast product is optionally injected into a body, which may be, for example, a human or animal body, but which may also be an inert body. The injection is performed in such a way that the contrast product is fixed at least temporarily in or passes through an observed zone 1. In the case of a human body, for example, the contrast product may be injected intravenously. The observed zone may then comprise a blood vessel through which the contrast product passes, and also the tissues that surround this vessel.

The body is placed in a system that surrounds a part of the body and that is capable of generating a high-amplitude magnetic induction $B_0$. This induction comprises gradients in principle directions in space according to the type of information that it is desired to acquire. For example, if it is desired to obtain magnetic resonance signals for elementary volumes in three-dimensional space, it will be advisable to introduce coding gradients $G_x$, $G_y$, and $G_z$ for the magnetic induction $B_0$ in three main perpendicular directions (x, y, and z) in space, in a manner known in itself. By means of this technique, magnetic induction values that are different between elementary volumes of the body are ensured.

The system in which the body is placed also has a transmitter of radio frequency wave pulse sequences in a range of adjustable frequencies that may be more or less selective, according to the duration of transmission of the corresponding waves. These RF waves are transmitted perpendicular to the direction of the magnetic induction $B_0$. When a wave is transmitted at a frequency corresponding to the proton resonance frequency, said protons are then taken out of their equilibrium position in a direction close to that of the induction $B_0$, and then they gradually return to this equilibrium position.

According to the disclosure, the protons in the observed zone have a resonance frequency that is shifted with respect to the usual Larmor frequency. Advantage is then taken of this particularity in order to recover electromagnetic signals only from these chemically shifted protons.

For this, at least two methods can be envisioned. According to a first embodiment, a radio frequency wave pulse sequence is transmitted with a frequency adjusted selectively to the value of the frequency shifted due to the chemical shift, i.e. $v_1$ according to the notation employed above.

At the end of each transmission of a radio frequency wave pulse sequence, a reception module detects and evaluates the transmitted magnetic resonance signal. For example, only the protons in a vessel come into resonance and generate a magnetic resonance signal.

Thus, if an image of the observed a zone is realized, for example in a spatial plane, by taking advantage of the magnetic induction gradients, and with each point of the image corresponding substantially to a detected signal value, as a function of its geographical position in the plane under consideration according to a conventional spatial coding, the zones where the contrast product has been fixed can be clearly distinguished. An image is thus obtained, where the vessel will be visible, while the tissues will be invisible.

This embodiment is therefore entirely advantageous. However, it has the drawback of requiring a sequence of radio frequency transmissions that are selective with respect to frequency, which means that a considerable transmission time is needed. When the observed zone is large, the signal acquisition time may prove to be disadvantageous.

A second advantageous embodiment makes it possible to limit the magnetic resonance signal acquisition time. It consists in using a radio frequency wave pulse transmission sequence comprising a first series of selective wave pulses adjusted to a frequency corresponding substantially to the Larmor frequency for the water protons not chemically shifted, i.e. the protons of the tissues in the example illustrated. These waves are transmitted with a sufficient duration to saturate the protons concerned, to such an extent that these protons no longer transmit any significant magnetic resonance signal at the end of the first series of wave pulses.

The radio frequency wave transmission sequence also comprises a second series of wave pulses that are relatively nonselective in terms of frequency, each wave of the sequence being transmitted over a short period of time. The range of frequencies covered by these waves comprises the resonance frequency of the chemically shifted protons, i.e. of the protons of the vessel. Thus, only the latter protons will come into resonance upon transmission of the second series of waves, the protons of the tissues being saturated. This makes it possible to receive rapidly the signals coming from only the protons of the vessel.

In this way, the signals transmitted by the chemically shifted protons are isolated with precision. Furthermore, contrast products used with dysprosium, praseodymium, or europium have only a limited action on the distortion of the magnetic induction in the observed zone, through the creation of magnetic induction microgradients, unlike gadolinium. The images obtained by applying this technique therefore potentially have a greater spatial resolution than the known techniques using gadolinium chelates.

As was described above, the chemical shift engendered by injection of contrast product, for example dysprosium, as a function of the concentration of the latter, is known. This prior knowledge can make it possible to select precisely the frequency of the wave to be transmitted in the observed zone. However, in another advantageous embodiment, it is possible to determine the frequency resulting from the chemical shift without prior knowledge. For this, the observed zone 1 of the body is subjected to successive waves in a broad spectrum of radiofrequencies and the magnetic resonance signals generated by the observed zone in reaction to each of these waves are detected. The main frequency that causes the protons of the observed zone having undergone the chemical shift to come into resonance is then deduced therefrom.

As disclosed herein, the observed zone may be taken to comprise a blood vessel surrounded by tissues. This representation makes it possible to envision applications of the present disclosure in the angiography field.

However, the disclosure can also be applied to other types of observed zones. In particular, the observed zone may comprise a target, which may, for example, be a cell, a molecule, a protein, or a group of targets of the body under consideration, such as a group of cells expressing a gene.

In this situation, a known targeting molecule is advantageously attached to contrast product injected into the body, such that the latter is temporarily fixed in the target. The steps described above can then be carried out so as to acquire magnetic resonance signals coming from the target only, with the exclusion of certain surrounding tissues in which the contrast product has not been fixed. This embodiment is particularly advantageous and finds applications in the field of cellular and molecular imaging, for example for studying gene expression in vivo, for localizing a particularly biological activity, or the like.

The observed zone may also be a zone of angiogenesis, for example a tumor zone. Such a zone generally comprises a vascularized network, the vascularization index of which gives an indication regarding the malignant or benign nature of the tissue.

In one embodiment, the system makes it possible to determine such a vascularization index. To this effect, the lanthanide chelate used as contrast product is injected so as to be temporarily fixed in the tissue zone. As described above, it is possible to realize a spectrum in this observed zone, i.e. to transmit successive radio frequency waves within a broad spectrum of frequencies. The resonance frequency of the protons located in the vascularized network present in the tissue zone is deduced therefrom, this resonance frequency being substantially the frequency for which magnetic resonance signals were received (outside the conventional Larmor frequency of the water protons not having experienced a chemical shift). Advantageously, this operation can be carried out several times at successive moments so as to make it possible to monitor any change in the time of this resonance frequency.

As was indicated above, the chemical shift caused by the contrast product, for example based on dysprosium, is proportional to the concentration of dysprosium. Determination of the resonance frequency in the tissue zone, which is itself proportional to the chemical shift, then gives an indication of the concentration of contrast product fixed in the observed zone. It is therefore understood that this indication constitutes a vascularization index that can be taken into account in a subsequent analysis of the tissue.

As in the previous cases, the magnetic resonance signals coming from the tissue zone can be acquired so as to characterize in greater detail the vascularized network present in the tissue zone. An image of the zone can also be obtained from this acquisition.

Magnetic resonance (MR) thermometry based on proton resonance frequency (PRF) shift can be used to monitor temperature changes in an area heated by HIFU in MRI-guided HIFU equipment, based on the phenomenon of the resonance frequency of the protons in water being offset (shifted) dependent on the temperature change. MR thermometry based on PRF-shift requires that a base image (MR phase image) before heating, also referred to as a reference image, be generated, with the reference image providing information on a reference phase. By subtraction from the phase image (also referred to as a heated image) acquired during heating or after heating, the exact value of the elevated temperature in the heated area can be determined.

During a practical heating process, after a reference image is acquired changes may occur in the position of the ultrasonic transducer (i.e. the treatment head), and the susceptibility change resulting from the movements of the ultrasonic transducer causes changes in the static magnetic field of the focal region of the ultrasonic transducer, so that the subtraction of the heated image and the reference image produces an additional phase difference, thus causing errors in the temperature measurement.

Currently, there are mainly two common solutions for reducing temperature errors. One of the solutions can be referred to as a single reference image method wherein, after the reference image has been acquired, the movement range of the ultrasonic transducer is restricted, so as to restrict the temperature errors within an acceptable range. However, since the spatial range used by a reference image is very small, while the ultrasonic transducer moves within a relatively large spatial range in the HIFU treatment process, it is necessary to acquire reference images frequently for various positions in order to measure the temperature of each focal position of the ultrasonic transducer, and this increases the complexity of the temperature measurement and the overall treatment time.

The other solution for reducing temperature errors can be referred to as a self-reference method, i.e. not acquiring any reference images, but instead utilizing the heated images themselves to obtain the reference phase by a polynomial fitting and extrapolation of the phase from the non-heated region. The temperature change monitored using this method may be limited to the vicinity of the focus of HIFU. Furthermore, the accuracy of the polynomial fitting and extrapolation and the complexity of the phase image are dependent on the size of the heated area, and it is relatively difficult to obtain stable, consistent, and accurate results in general.

Incorporated herein by reference are the following US applications and/or publications: US Pub. No. 2009/0275821, published on May 5, 2008; US Pub. No. 2006/0058642, published on Mar. 16, 2006; US Pub. No. 2010/0217114, published on Aug. 26, 2010.

Another method is self-referencing or reference-less thermometry. In this method, tissue outside the therapeutic zone (tissue being heated) is used to measure the PRFS. Assuming this tissue does not heat, then the PRFS in these regions is due only to changes in magnetic field.

As used herein, "thermal level" includes absolute temperature, relative temperature, temperature change, heat, change in heat, relative heat, thermal dosage, and other metrics related to thermal conditions.

Another method is use of nearby fat tissue as a reference. Fat tissue does not experience a PRFS with thermal level change, so that any thermal level-induced changes in PRF are due to background field changes.

According to some embodiments, a system for performing renal nerve ablation comprises a HIFU device for heating targeted tissue and a MRI device for monitoring thermal levels in one or more volumetric zones.

Figure 1:
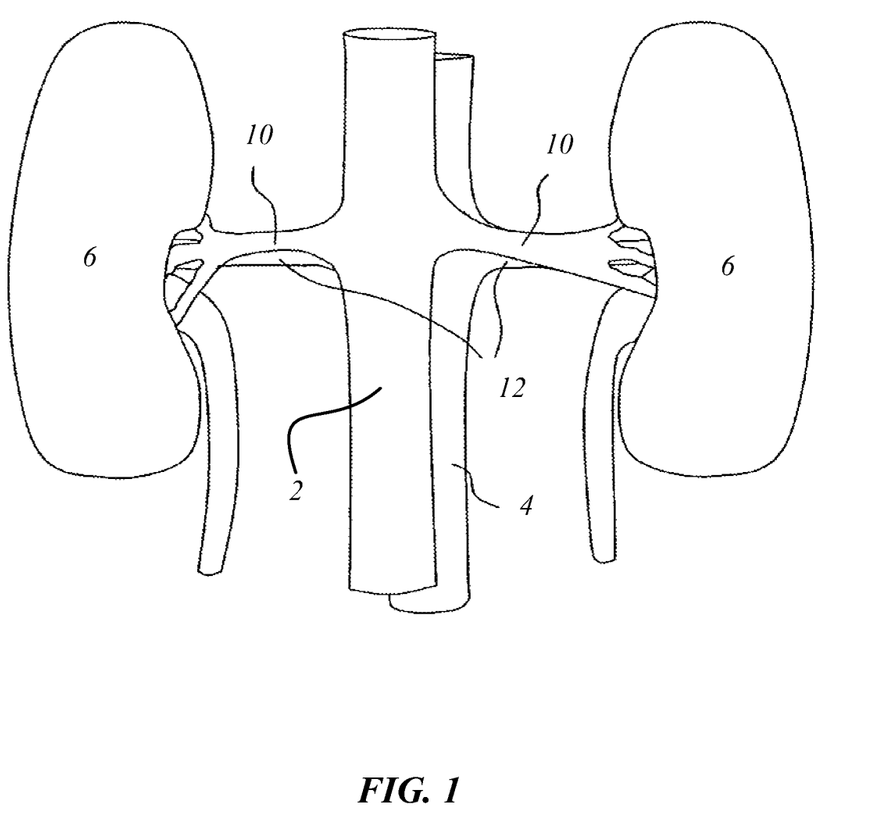
FIG. 1 shows a view of portions of a patient's anatomy.
Figure 2:
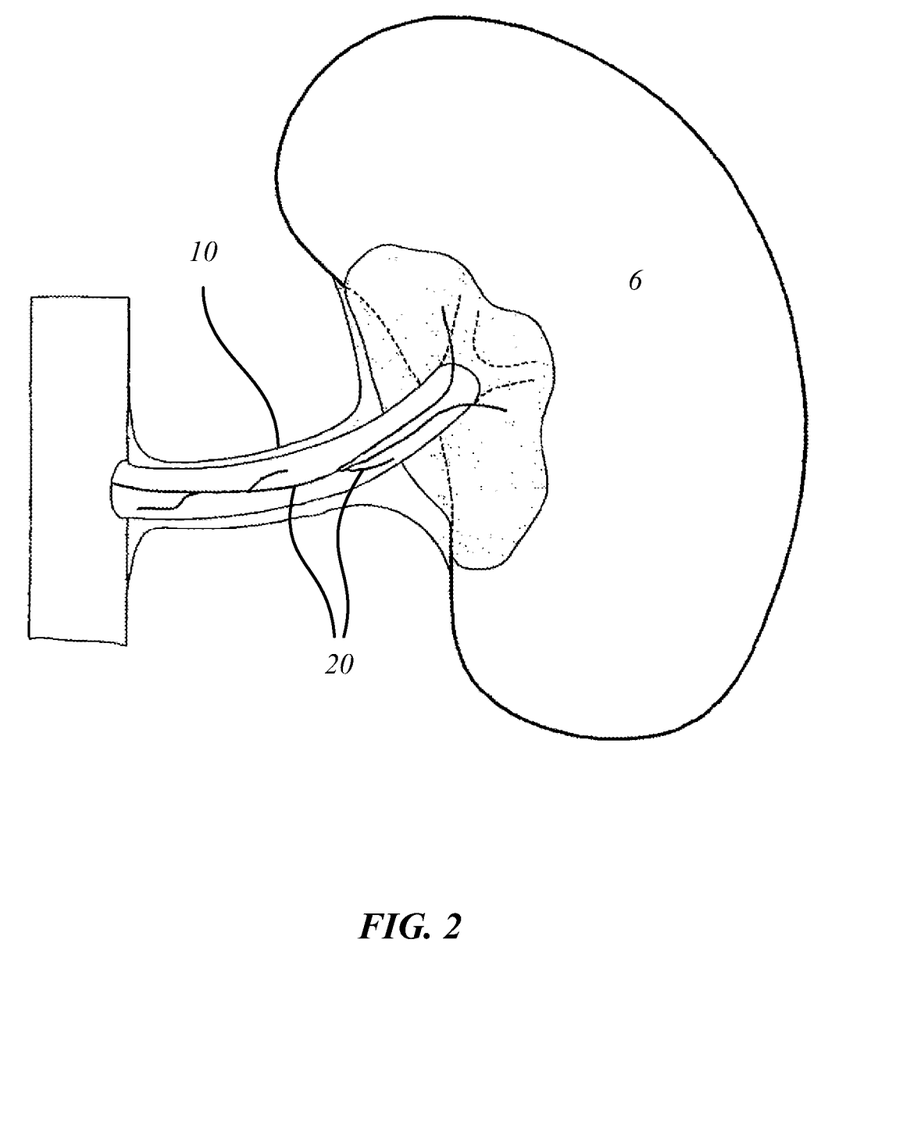
FIG. 2 shows a view of portions of a patient's anatomy.
Figure 3:
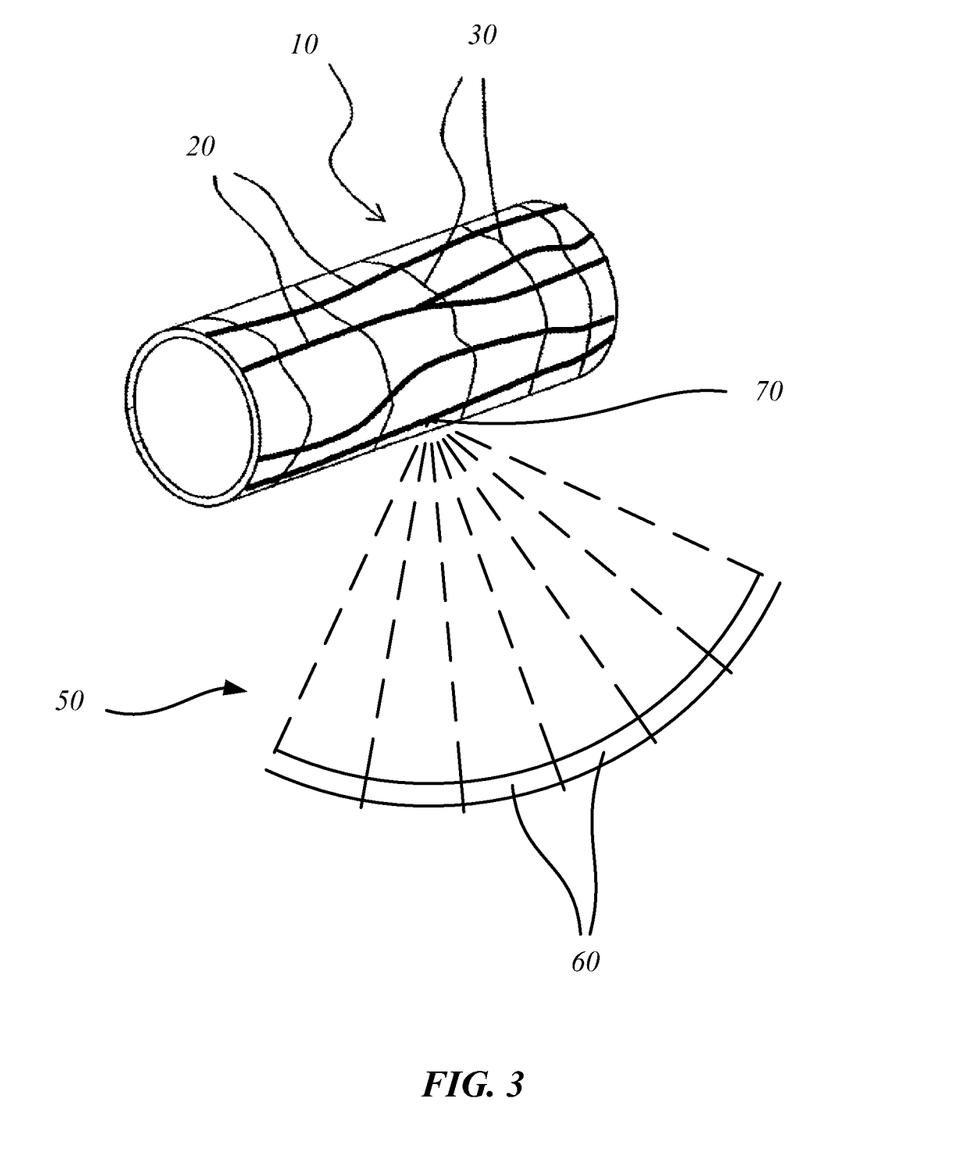
FIG. 3 shows a view of an array of transducers focused on a renal nerve (not to scale), according to some embodiments of the present disclosure.

According to some embodiments, as shown in FIG. 3, a HIFU device 50 may comprise one or more transducers 60 for emitting ultrasound energy. Where a HIFU device 50 comprises an array of transducers 60 is provided, constituent transducers 60 of the array may be directed to converge generally at a focal region 70. The focal region 70 may be determined by position of the constituent transducers 60 relative to each other or position of the array relative to a target site 70.

According to some embodiments, an MRI device 150 is used to dynamically monitor tissue heating as well as detect the points at which desired irreversible damage of targeted tissue is achieved. According to some embodiments, an MRI device 150 employing one or more of the above referenced methods is provided to monitor one or more thermal levels in one or more volumetric zones. For example, RF coil configurations designed to operate according to the methods disclosed herein are used to monitor or infer lesion formation.

Figure 4:
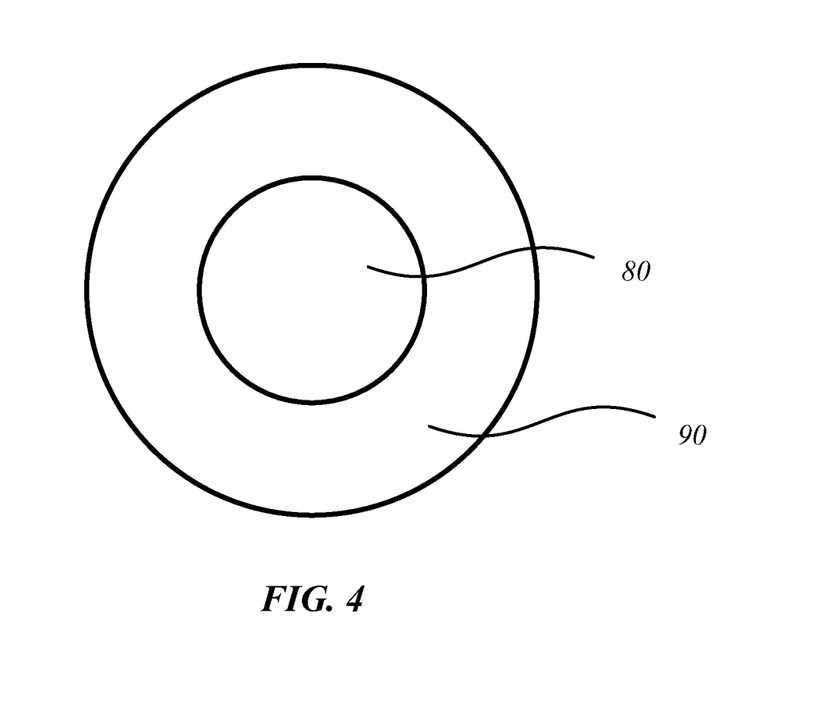
FIG. 4 shows a plurality of volumetric zones, according to some embodiments of the present disclosure.
Figure 5:
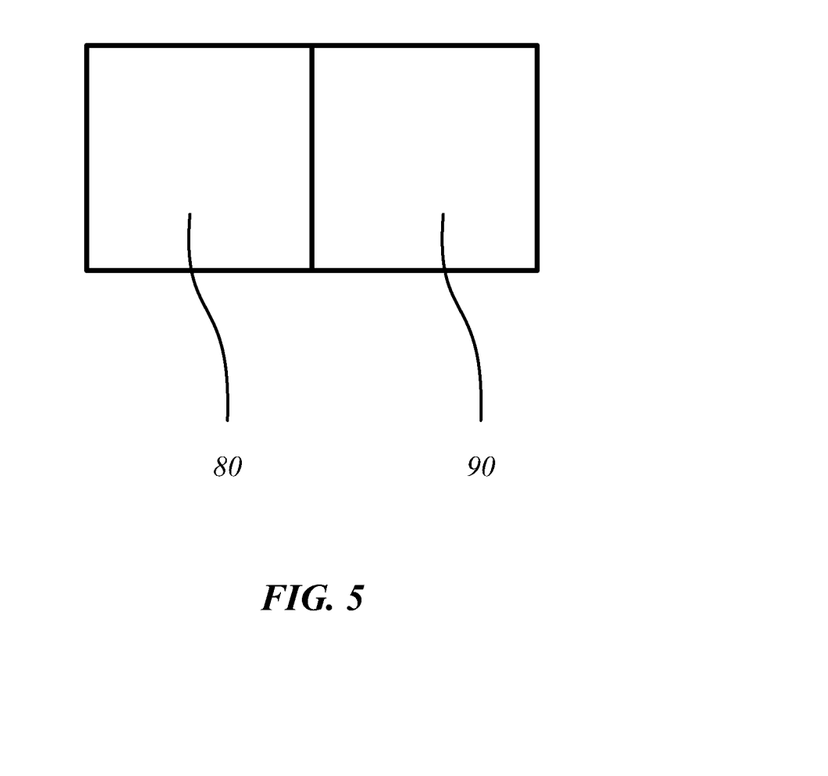
FIG. 5 shows a plurality of volumetric zones, according to some embodiments of the present disclosure.

According to some embodiments, as shown in FIG. 4, a first volumetric zone 80 may be concentric within a second volumetric zone 90. According to some embodiments, as shown in FIG. 5, a first volumetric zone 80 may be adjacent to a second volumetric zone 90. Other arrangements are contemplated, including overlapping, nearby, connected, or spaced apart volumetric zones. Volumetric zones may take any shape or size.

Figure 6:
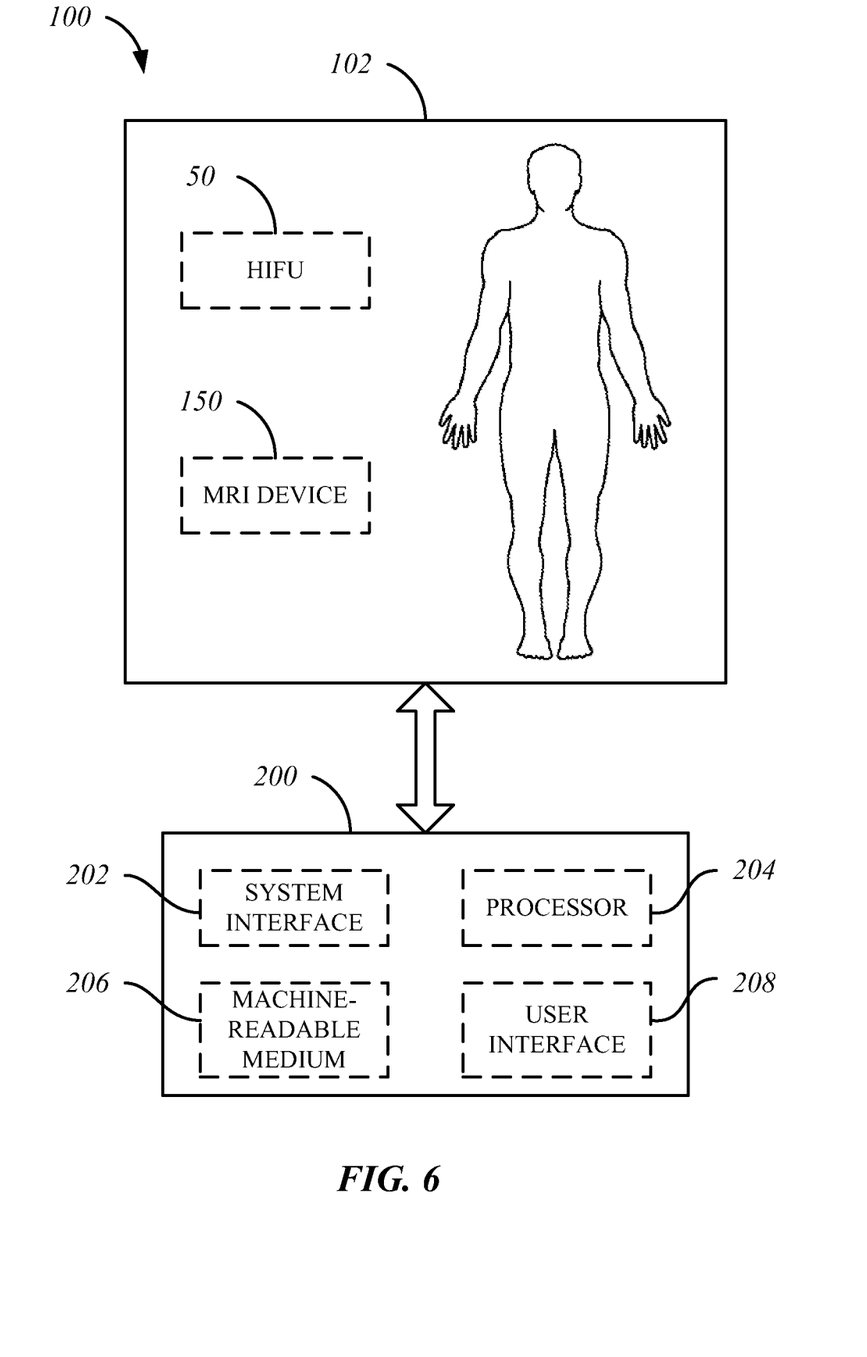
FIG. 6 shows a block diagram of a MRI-guided ultrasound system, according to some embodiments of the present disclosure.

According to some embodiments, as shown in FIG. 6, an ablation system 100 may comprise an operation system 102 and a control system 200. Operation system 102 may comprise a HIFU device 50 and an MRI device 150 for performing operations on a patient. According to some embodiments, a control system 200 is provided to control, monitor, or interact with one or more components of operation system 102, such as HIFU device 50 and MRI device 150.

According to some embodiments, as shown in FIG. 6, a control system 200 may comprise a system interface 202, a processor 204, a machine-readable medium 206, a user interface 208, and other components as appropriate to produce the desired functionalities of the control system 200.

The control system 200 may include a processor 204 for executing instructions and may further include a machine-readable medium 206, such as a volatile or non-volatile memory, for storing data and/or instructions for software programs. The instructions, which may be stored in a machine-readable medium 206, may be executed by the control system 200 to control and manage access to the various networks, as well as provide other communication and processing functions. The instructions may also include instructions executed by the control system 200 for various user interface devices, such as a display and a keypad. The control system 200 may include an input port and an output port. Each of the input port and the output port may include one or more ports. The input port and the output port may be the same port (e.g., a bi-directional port) or may be different ports.

The control system 200 may be implemented using software, hardware, or a combination of both. By way of example, the control system 200 may be implemented with one or more processors. A processor may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, or any other suitable device that can perform calculations or other manipulations of information.

A machine-readable medium can be one or more machine-readable media. Software shall be construed broadly to mean instructions, data, or any combination thereof, whether referred to as software, firmware, middleware, microcode, hardware description language, or otherwise. Instructions may include code (e.g., in source code format, binary code format, executable code format, or any other suitable format of code).

Machine-readable media may include storage integrated into a processing system, such as might be the case with an ASIC. Machine-readable media may also include storage external to a processing system, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, or any other suitable storage device. Those skilled in the art will recognize how best to implement the described functionality for the control system 200. According to one aspect of the disclosure, a machine-readable medium is a computer-readable medium encoded or stored with instructions and is a computing element, which defines structural and functional interrelationships between the instructions and the rest of the system, which permit the instructions' functionality to be realized. In one aspect, a machine-readable medium is a non-transitory machine-readable medium, a machine-readable storage medium, or a non-transitory machine-readable storage medium. In one aspect, a computer-readable medium is a non-transitory computer-readable medium, a computer-readable storage medium, or a non-transitory computer-readable storage medium. Instructions may be executable, for example, by a client device or server or by a processing system of a client device or server. Instructions can be, for example, a computer program including code.

An interface (e.g., 202) may be any type of interface and may reside between any of the components shown in FIG. 6. An interface may also be, for example, an interface to the outside world (e.g., an Internet network interface). A transceiver block may represent one or more transceivers, and each transceiver may include a receiver and a transmitter. A functionality implemented in a control system 200 may be implemented in a portion of a receiver, a portion of a transmitter, a portion of a machine-readable medium, a portion of a display, a portion of a keypad, or a portion of an interface, and vice versa.

According to some embodiments, an MRI device 150 for guiding HIFU operation comprises, in combination, at least one RF coil designed to receive signals from tissues such as muscle, glandular tissue, and fat (among other tissues). An MRI pulse sequence is provided to obtain images that measure temperature in the tissues.

According to some embodiments, an MRI device 150 for guiding HIFU operation comprises at least one of a coil that generates a static magnetic field, a RF coil, an x-gradient coil, a y-gradient coil, and a z-gradient coil. One or more coils allow sequences of currents to acquire PRF measurements and sequences to acquire T1 weighted images. There are several MRI methods may be used for measuring thermal levels using well-known MRI parameters, such as the spin-lattice relaxation time ("T1"). Sequence parameters—such as the time to repeat ("TR"), the time to echo ("TE"), and the flip angle—may be chosen by the user. For example, thermal level maps can be generated based on such procedures that provide T1 derived images evaluated with fast spoiled gradient echo sequences applied during the actual thermal therapy exposure. The parameters used are to some degree based on the tissue type and the precise evaluation of the behavior due to physiological or metabolic changes in the tissue during thermal therapy exposure. For example, TE, TR, and the flip angle of the spoiled gradient echo may be specified in the sequence.

Figure 7:
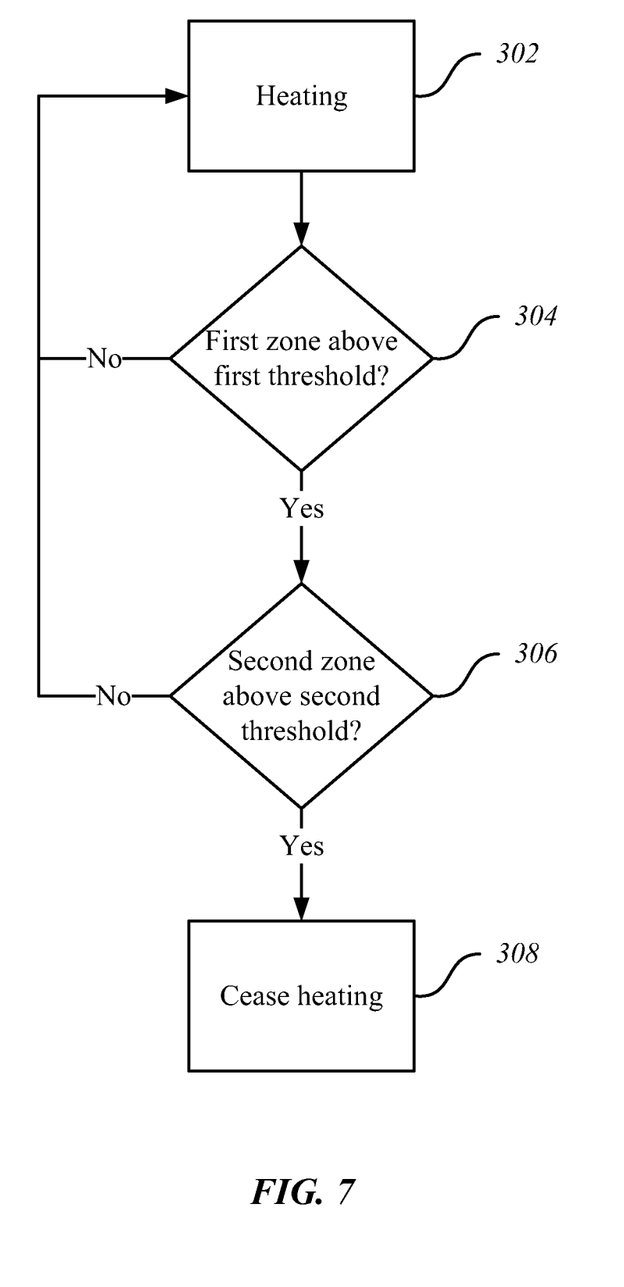
FIG. 7 shows a flowchart of an operation of a MRI-guided ultrasound system, according to some embodiments of the present disclosure.

According to some embodiments, as shown in FIG. 7, a method of treating hypertension in a mammal comprises: by focused sound energy, heating at least one nerve at a surface of a renal artery in a mammal, as shown in operation 302. The method includes, as shown in operations 304 sand 306, during the heating and by magnetic resonance imaging, repeatedly determining thermal levels in each of a first volumetric zone 80 and a second volumetric zone 90 of a region that includes at least a portion of the surface, the second zone 90 being adjacent to the first zone 80.

According to some embodiments, as shown in FIG. 7, a method includes, after a thermal level in the first zone 80 exceeds a first threshold, and/or after a thermal level in the second zone 90 exceeds a second threshold, ceasing the heating as shown in operation 308. According to some embodiments, the method includes, after a thermal level in the first zone 80 exceeds a first threshold, and/or after a thermal level in the second zone 90 exceeds a second threshold, heating a different zone in a subsequent heating operation. The target of a first heating operation and a subsequent heating operation may define a pathway. For example, heating a different zone may comprise moving a focal point of the focused sound energy. The focal point may be moved while delivery of heat continues, or the focal point may be moved after heating is ceased. The first threshold and the second threshold may correspond to respective thermal levels that are indicative of a desired effect on renal nerves, for example. According to some embodiments, the method includes, after a thermal level in the first zone 80 exceeds a first threshold, or after a thermal level in the second zone 90 exceeds a second threshold, ceasing the heating.

According to some embodiments, a method includes, after a thermal level in the first zone 80 is within a first range, and after a thermal level in the second zone 90 is within a second range, ceasing the heating. The first range and the second range may correspond to respective thermal levels that are indicative of desired effect on renal nerves, for example. According to some embodiments, the method includes, after a thermal level in the first zone 80 is within a first range, or after a thermal level in the second zone 90 is within a second range, ceasing the heating.

According to some embodiments, a method includes heating a different nerve at the surface of the renal artery or a different portion of the same nerve. This may be accomplished by moving the focal region of an array of transducers.

Figure 8:
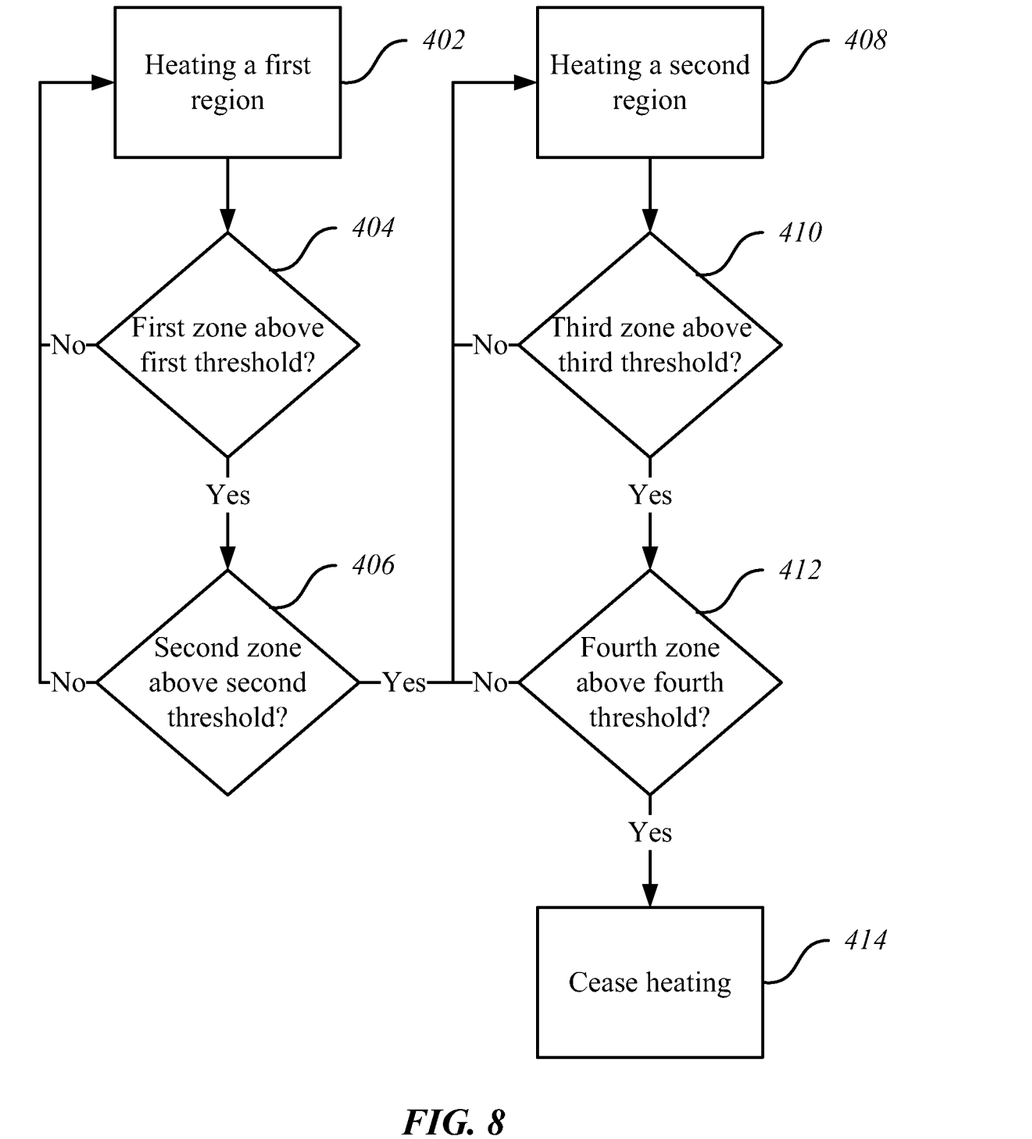
FIG. 8 shows a flowchart of an operation of a MRI-guided ultrasound system, according to some embodiments of the present disclosure.

For example, according to some embodiments, as shown in FIG. 8, heating is provided to a first region, as shown in operation 402. During the heating and by magnetic resonance imaging, thermal levels in each of first and second volumetric zones of the first region are monitored, as shown in operations 404 and 406. After an indicium of a thermal level in the first zone exceeds a first threshold, and after an indicium of a thermal level in the second zone exceeds a second threshold, heating may be provided to a second region of the at least one nerve, as shown in operation 408. During the heating and by magnetic resonance imaging, thermal levels in each of third and fourth volumetric zones of the second region are monitored, as shown in operations 410 and 412. After an indicium of a thermal level in the third zone exceeds a third threshold, and after an indicium of a thermal level in the fourth zone exceeds a fourth threshold, heating may be ceased, as shown in operation 414. The first region and the second region may, together, define a pathway or a portion of a pathway. Heating may be continuously provided or temporarily ceased as the focal point of the heating device moves along the pathway.

According to some embodiments, application of focused sound energy to points around an artery has the result that sympathetic nerves are damaged and the artery is not damaged. The temperature of the artery may be substantially maintained by blood flow through the artery during the procedure while temperature of at least one nerve is elevated. Tissue near the nerves and the artery may be monitored by MRI or other means, whereby delivery of heat may be ceased when a thermal level exceeds a threshold.

According to some embodiments, a cooling catheter may be provided within the artery in a vicinity of the focal region of the focused sound energy. The cooling catheter provides maintenance of reduction of thermal levels in or around the artery to reduce or eliminate damage to the artery. According to some embodiments, a catheter may be provided at, along, or aligned with a target location within an artery. The catheter may provide a localizing signal to an MRI scanner or other device to identify the target location. The target location may identify where a focal point of the focused sound energy should be applied.

According to some embodiments, the method includes, as a result of the heating, lowering a blood pressure in the mammal. According to some embodiments, devices and methods disclosed herein may be used to treat Congestive Heart Failure ("CHF") or related conditions, including hypertension.

CHF may occur when the heart becomes damaged and reduces blood flow to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system. It is believed that progressively decreasing perfusion of the kidneys is a principal non-cardiac cause perpetuating a downward spiral of CHF.

In addition to their role in the progression of CHF, the kidneys play a significant role in the progression of Chronic Renal Failure ("CRF"), End-Stage Renal Disease ("ESRD"), hypertension (pathologically high blood pressure) and other cardio-renal diseases. The functions of the kidneys can be summarized under three broad categories: filtering blood and excreting waste products generated by the body's metabolism; regulating salt, water, electrolyte, and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to deteriorate further as fluids are retained and blood toxins accumulate due to the poorly functioning kidneys.

It has been established in animal models that the heart failure condition results in abnormally high sympathetic activation of the kidneys. An increase in renal sympathetic nerve activity leads to decreased removal of water and sodium from the body, as well as increased renin secretion. Increased renin secretion leads to vasoconstriction of blood vessels supplying the kidneys, which causes decreased renal blood flow. Reduction of sympathetic renal nerve activity, e.g., via renal nerve ablation, may reverse or ameliorate processes.

According to embodiments, heating may be ceased for a period of time between any ablation procedure and a subsequent procedure on ipsilateral renal nerves. For example, a time period may be sufficient to allow inflammation to recede, scar tissue to begin forming, blood pressure to equilibrate, and any compensatory hypertensive effect from the contralateral kidney to manifest. For example, the time period may be greater or less than 1 day, 10 days, 100 days, and 1000 days. By further example, the time period may be equal to or greater than 1, 2, 3, 4, 5, 6, 7, 10, 15, 30, 60, 90, 120, or 180 days. By further example, the time period may be equal to or greater than 1, 2, 3, 4, 5, 6, 7, 8, 9, 10, 11, 12, 18, or 24 months.

According to some embodiments, devices and methods disclosed herein may be used in conjunction or combination with other devices and methods for achieving renal neuromodulation, including localized drug delivery (such as by a drug pump or infusion catheter), stimulation electric field, and laser therapy, inter alia.

Incorporated herein by reference are the following US applications and/or publications: US Pub. No. 2010/0057150, published on Mar. 4, 2010; US Pub. No. 2010/0222854, published on Sep. 2, 2010; US Pub. No. 2008/0213331, published on Sep. 4, 2008.

As used herein, the term "software module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the invention have been described, these have been presented by way of example only, and are not intended to limit the scope of the invention. Indeed, the novel methods and systems described herein may be embodied in a variety of other forms without departing from the spirit thereof. The accompanying claims and their equivalents are intended to cover such forms or modifications as would fall within the scope and spirit of the invention.

What is claimed is:

1. A method of treating hypertension in a mammal, comprising:
    by focused sound energy, heating at least one nerve at a surface of a renal artery in a mammal;
    during the heating and by magnetic resonance imaging, repeatedly determining thermal levels in each of a first volumetric zone and a second volumetric zone within a target region that includes at least a portion of the surface and is subject to the heating;
    after determining that an indicium of a thermal level in the first zone exceeds a first threshold, and upon determining that an indicium of a thermal level in the second zone exceeds a second threshold, different from the first threshold, ceasing the heating of the at least one nerve for at least one day; and
    as a result of the heating, lowering a blood pressure in the mammal.

2. The method of claim 1, wherein the first zone is substantially concentric with the second zone.

3. The method of claim 1, wherein the magnetic resonance imaging comprises a proton resonance frequency acquisition sequence.

4. The method of claim 1, wherein the heating is ceased for at least four months.

5. The method of claim 1, wherein the heating is ceased for at least six months.

6. The method of claim 1, wherein the heating is ceased for at least 12 months.

7. The method of claim 1, wherein the second zone is adjacent to the first zone.

8. A method of treating hypertension in a mammal, comprising:
    by focused sound energy, heating a first region of at least one nerve at a surface of a renal artery in a mammal;
    during the heating and by magnetic resonance imaging, repeatedly determining thermal levels in each of a first volumetric zone and a second volumetric zone within the first region that includes at least a portion of the surface and is subject to the heating of the first region;
    after determining that an indicium of a thermal level in the first zone exceeds a first threshold, and upon determining that an indicium of a thermal level in the second zone exceeds a second threshold, different from the first threshold, heating a second region of the at least one nerve by focused sound energy;
    during the heating and by magnetic resonance imaging, repeatedly determining thermal levels in each of a third volumetric zone and a fourth volumetric zone of the second region that includes at least a portion of the surface and is subject to the heating of the second region;
    after determining that an indicium of a thermal level in the third zone exceeds a third threshold, and upon determining that an indicium of a thermal level in the fourth zone exceeds a fourth threshold, different from the third threshold, ceasing the heating of the at least one nerve for at least one day; and
    as a result of the heating, lowering a blood pressure in the mammal.

9. The method of claim 8, wherein the third zone is substantially concentric with the fourth zone.

10. The method of claim 8, wherein the first region and the second region defines a pathway.

11. The method of claim 8, wherein the heating is ceased for at least four months.

12. The method of claim 8, wherein the heating is ceased for at least six months.

13. The method of claim 8, wherein the heating is ceased for at least 12 months.

14. The method of claim 8, wherein the second zone is adjacent to the first zone and wherein the fourth zone is adjacent to the third zone.

15. A system for performing renal nerve ablation, comprising:
    a HIFU device comprising at least one ultrasound transducer and configured to heat a targeted tissue at a focal region of the array;
    a MRI device programmed to monitor thermal levels in a plurality of volumetric zones; and a control system having instructions for:
> by the HIFU device, heating the targeted tissue;
>
> during the heating and by the MRI device, repeatedly determining thermal levels in each of a first volumetric zone and a second volumetric zone within a target region that includes the targeted tissue and is subject to the heating;
>
> after determining that an indicium of a thermal level in the first zone exceeds a first threshold, and upon determining that an indicium of a thermal level in the second zone exceeds a second threshold, different from the first threshold, ceasing the heating of the targeted tissue for at least one day.

16. The system of claim 15, wherein the first zone is substantially concentric with the second zone.

17. The system of claim 15, wherein the MRI device comprises at least one RF coil that allows sequences of currents to acquire images.

18. The system of claim 15, wherein the second zone is adjacent to the first zone.

* * * * *